United States Patent
Robinson et al.

(10) Patent No.: US 11,259,968 B2
(45) Date of Patent: *Mar. 1, 2022

(54) FLEXIBLE, ADHERENT, AND NON-POLYURETHANE FILM WOUND DRAPE COVER

(71) Applicant: KCI Licensing, Inc., San Antonio, TX (US)

(72) Inventors: Timothy Mark Robinson, Shillingstone (GB); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 420 days.

This patent is subject to a terminal disclaimer.

(21) Appl. No.: 16/360,601

(22) Filed: Mar. 21, 2019

(65) Prior Publication Data

US 2019/0216652 A1    Jul. 18, 2019

Related U.S. Application Data

(63) Continuation of application No. 15/387,928, filed on Dec. 22, 2016, now Pat. No. 10,278,870, which is a
(Continued)

(51) Int. Cl.
*A61F 13/02* (2006.01)
*A61F 13/00* (2006.01)
(Continued)

(52) U.S. Cl.
CPC .... *A61F 13/0253* (2013.01); *A61F 13/00068* (2013.01); *A61F 13/0203* (2013.01);
(Continued)

(58) Field of Classification Search
CPC .............. A61F 13/0253; A61F 13/0203; A61F 13/0269; A61F 13/00068; A61F 13/0289; A61M 1/90
See application file for complete search history.

(56) References Cited

U.S. PATENT DOCUMENTS 1,355,846 A    10/1920    Rannells
2,547,758 A     4/1951    Keeling
(Continued)

FOREIGN PATENT DOCUMENTS

AU    550575 B2    3/1986
AU    745271 B2    3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Adam Marcetich

(57) ABSTRACT

A system for treating a tissue site includes a reduced-pressure source to apply reduced pressure, a manifold in fluid communication with the pressure source to provide reduced pressure to the tissue site, and a drape for adhering to the tissue site to cover the tissue site and the manifold. The drape includes an adhesive layer for sealing the drape to the tissue site to create a sealed space having the manifold therein, and a non-adhesive layer formed from a portion of the adhesive layer. A method for manufacturing a medical drape includes providing a sheet of adhesive material and treating a side of the sheet of adhesive material to form a non-adhesive layer and an adhesive layer. The method laminates a release liner adjacent the adhesive layer.

20 Claims, 5 Drawing Sheets

Related U.S. Application Data continuation of application No. 14/080,199, filed on Nov. 14, 2013, now Pat. No. 9,561,135.

(60) Provisional application No. 61/748,395, filed on Jan. 2, 2013.

(51) Int. Cl.

| | |
|---|---|
| *B29C 59/14* | (2006.01) |
| *A61M 1/00* | (2006.01) |
| *A61L 15/26* | (2006.01) |
| *A61L 15/58* | (2006.01) |
| *C08L 83/04* | (2006.01) |
| *C09J 183/04* | (2006.01) |
| *B29L 31/26* | (2006.01) |
| *B29L 31/00* | (2006.01) |

(52) U.S. Cl.
CPC ...... *A61F 13/0269* (2013.01); *A61F 13/0289* (2013.01); *A61L 15/26* (2013.01); *A61L 15/58* (2013.01); *A61M 1/90* (2021.05); *B29C 59/14* (2013.01); *B29L 2031/26* (2013.01); *B29L 2031/753* (2013.01); *C08L 83/04* (2013.01); *C09J 183/04* (2013.01); *Y10T 428/28* (2015.01); *Y10T 428/2852* (2015.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,522,870 A | 6/1985 | Esmay |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,562,091 A | 12/1985 | Sachdev et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,751,108 A | 6/1988 | Larimore et al. |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,525,422 A | 6/1996 | Spies et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 5,782,496 A | 7/1998 | Casper et al. |
| 6,071,267 A | 6/2000 | Zamierowski |
| 6,135,116 A | 10/2000 | Vogel et al. |
| 6,187,834 B1 | 2/2001 | Thayer et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,579,585 B1 * | 6/2003 | Garvic .............. G09F 3/10 283/101 |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,259,905 B2 | 2/2016 | Wilken et al. |
| 9,289,542 B2 | 3/2016 | Blott et al. |

(56) References Cited

U.S. PATENT DOCUMENTS

| | | | |
|---|---|---|---|
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0155243 A1 | 10/2002 | Kobe et al. | |
| 2003/0054138 A1 | 3/2003 | Stebbings et al. | |
| 2005/0256251 A1 | 11/2005 | Amano et al. | |
| 2006/0068013 A1 | 3/2006 | DiTizio et al. | |
| 2007/0136966 A1 | 6/2007 | Aubourg et al. | |
| 2007/0249981 A1* | 10/2007 | Hurwitz | A61F 13/0203 602/58 |
| 2007/0275238 A1 | 11/2007 | Moretti et al. | |
| 2008/0187693 A1 | 8/2008 | Nielsen | |
| 2009/0092843 A1 | 4/2009 | Arlt et al. | |
| 2009/0280322 A1 | 11/2009 | Daniels et al. | |
| 2010/0036488 A1 | 2/2010 | de Juan, Jr. et al. | |
| 2010/0069858 A1 | 3/2010 | Olson | |
| 2010/0112345 A1 | 5/2010 | Sieber et al. | |
| 2010/0151236 A1 | 6/2010 | Holubka et al. | |
| 2011/0120477 A1 | 5/2011 | Henderson et al. | |
| 2011/0206923 A1 | 8/2011 | Liu et al. | |
| 2011/0224593 A1 | 9/2011 | Tunius | |
| 2011/0262523 A1* | 10/2011 | Zhu | A61L 15/24 424/448 |
| 2012/0308754 A1* | 12/2012 | Dehlinger | C09J 7/22 428/41.8 |
| 2012/0329956 A1 | 12/2012 | Prenzel et al. | |
| 2013/0017246 A1 | 1/2013 | Tunius | |
| 2013/0019569 A1* | 1/2013 | Epstein | A61F 13/0276 53/452 |
| 2014/0163491 A1 | 6/2014 | Schuessler et al. | |
| 2014/0178681 A1 | 6/2014 | Wright et al. | |
| 2014/0378608 A1 | 12/2014 | Yang et al. | |
| 2015/0080788 A1 | 3/2015 | Blott et al. | |

FOREIGN PATENT DOCUMENTS

| | | | |
|---|---|---|---|
| AU | 755496 B2 | 12/2002 | |
| CA | 2005436 A1 | 6/1990 | |
| CN | 103505324 A * | 1/2014 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| GB | 2423267 A | 8/2006 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | 2007030601 A2 | 3/2007 | |
| WO | 2009055251 A1 | 4/2009 | |
| WO | WO-2009133175 A1 * | 11/2009 | C09J 7/21 |
| WO | 2009146441 A1 | 12/2009 | |
| WO | 2010033574 A1 | 3/2010 | |
| WO | 2010056541 A1 | 5/2010 | |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, p. 634-639.

Orringer, Jay, et al.; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al.; "Vacuum Treatment in the Surgical Management of Purulent Wounds"; Vestnik Khirurgi, Sep. 1986, pp. 18-21 and 6 page English translation thereof.

Davydov, Yu. A., et al.; "Vacuum Therapy in the Treatment of Purulent Lactation Mastitis"; Vestnik Khirurgi, May 14, 1986, pp. 66-70, and 9 page English translation thereof.

Yusupov. Yu.N., et al.; "Active Wound Drainage", Vestnki Khirurgi, vol. 138, Issue 4, 1987, and 7 page English translation thereof.

Davydov, Yu.A., et al.; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 2.

Svedman, P.: "Irrigation Treatment of Leg Ulcers", The Lancet, Septembers, 1983, pp. 532-534.

Chinn, Steven D et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.

(56) References Cited

OTHER PUBLICATIONS

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

European Search Report corresponding to EP161198542.9, dated Feb. 20, 2017.

Australian Office Action for corresponding application AU87918AUP00, dated Jul. 5, 2017.

Notice of Rejection corresponding to Japanese Patent Application No. 2015-550386, dated Oct. 3, 2017.

Extended European Search Report for corresponding Application No. 181662990, dated May 24, 2018.

\* cited by examiner

US 11,259,968 B2

FLEXIBLE, ADHERENT, AND NON-POLYURETHANE FILM WOUND DRAPE COVER

This application is a continuation of U.S. patent application Ser. No. 15/387,928, entitled "Flexible, Adherent, and Non-Polyurethane Film Wound Drape Cover," filed Dec. 22, 2016, which is a continuation of U.S. patent application Ser. No. 14/080,199, entitled "Flexible, Adherent, and Non-Polyurethane Film Wound Drape Cover," filed Nov. 14, 2013, now U.S. Pat. No. 9,561,135, which claims the benefit, under 35 USC § 119(e), of the filing of U.S. Provisional Patent Application Ser. No. 61/748,395, entitled "Flexible, Adherent, and Non-Polyurethane Film Wound Drape Cover," filed Jan. 2, 2013, by Locke et al., which is incorporated herein by reference for all purposes.

FIELD

The present disclosure relates generally to dressings for adhering to a patient and, more particularly, but without limitation, to a drape formed of an adhesive layer having a non-adhesive layer formed from the adhesive layer.

BACKGROUND

Clinical studies and practice have shown that providing reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative-pressure therapy," "reduced-pressure therapy," or "vacuum therapy") provides a number of benefits, which may include faster healing and increased formulation of granulation tissue. In applying reduced-pressure therapy, typically a foam pad or other manifold is placed proximate the wound, covered with a drape to form a sealed space, and reduced pressure applied to the sealed space. If the drape leaks, additional energy may be required to overcome the leak and maintain therapeutic level of reduced pressure.

SUMMARY

These and other problems are generally solved or circumvented, and technical advantages are generally achieved, by embodiments that provide a medical drape formed of an adhesive layer having a de-tackified upper portion and a process to manufacture the same.

According to an illustrative, non-limiting embodiment, a system for treating a tissue site is described. The system can include a reduced-pressure source configured to apply reduced pressure and a manifold in fluid communication with the reduced-pressure source and configured to distribute reduced pressure to the tissue site. The system may also include a drape. The drape may have an adhesive layer formed of silicone having a thickness greater than about 100 microns. The adhesive layer may have a first surface and a second surface. The drape may also have a plasma layer having a thickness of about 5 microns formed by treating the first surface of the adhesive layer with a plasma treatment process. The second surface of the adhesive layer is configured to adhere at least to the tissue site and cover the manifold to create a sealed space over the manifold within the tissue site.

According to another illustrative embodiment, a dressing for treating a tissue site is described. The dressing includes a manifold having a plurality of flow channels configured to distribute reduced pressure to the tissue site and a drape. The drape may include an adhesive layer formed of silicone and having a thickness greater than about 100 microns. The adhesive layer may have a first surface and a second surface. The drape may also include a plasma layer having a thickness of about 5 microns formed by treating the first surface of the adhesive layer with a plasma treatment process. The second surface of the adhesive layer is configured to adhere at least to the tissue site and cover the manifold to create a sealed space over the manifold within the tissue site.

According to yet another illustrative embodiment, a method for manufacturing a medical drape can include providing a sheet of adhesive material having a first surface, a second surface, and a thickness greater than about 100 microns. The method may treat the first surface of the sheet of adhesive material with a plasma treatment process to form a plasma layer having a thickness of about 5 microns on the first surface of the sheet of adhesive material and an adhesive layer on the second surface of the sheet of adhesive material. The method may laminate a release liner adjacent the second surface of the adhesive material According to still another illustrative embodiment, a medical drape having a plasma layer on a first side of the medical drape and an adhesive layer on a second side of the medical drape, the plasma layer being formed from a portion of the adhesive layer is described. The medical drape may be produced by a process comprising the steps of providing a sheet of adhesive material having a first surface, a second surface, and a thickness greater than about 100 microns. The process may treat the first surface of the sheet of adhesive material with a plasma treatment process to form a plasma layer having a thickness of about 5 microns on the first surface of the sheet of adhesive material and an adhesive layer on the second surface of the sheet of adhesive material. The process may laminate a release liner adjacent the second surface of the adhesive material.

Other aspects, features, and advantages of the illustrative embodiments will become apparent with reference to the drawings and detailed description that follow.

BRIEF DESCRIPTION OF THE DRAWINGS

Illustrative embodiments are described in detail below with reference to the attached figures, which are incorporated by reference herein, and wherein.

DETAILED DESCRIPTION OF ILLUSTRATIVE EMBODIMENTS

New and useful systems, methods, and apparatuses associated with medical drapes that may be used with reduced-pressure therapy systems are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

Figure 1:
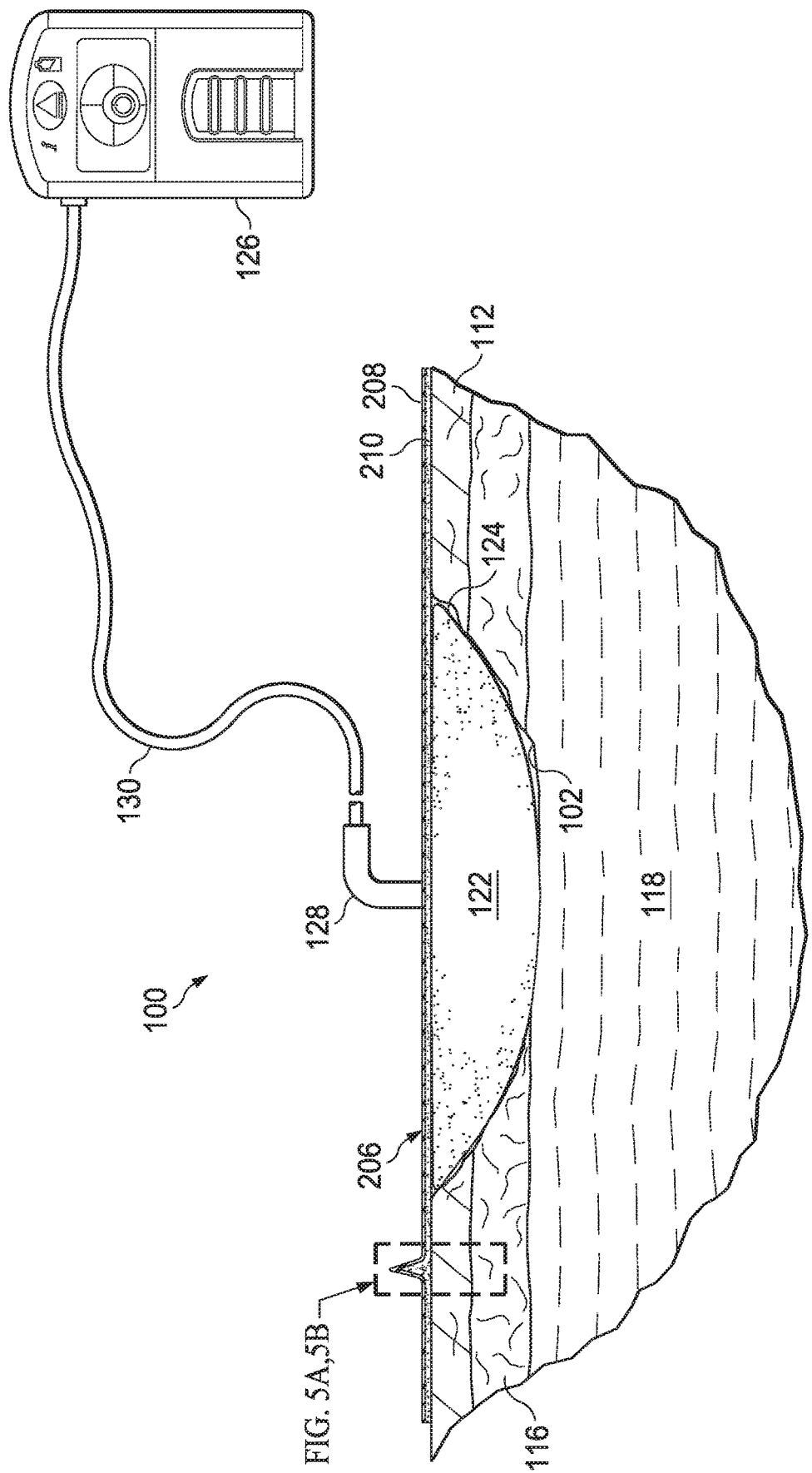
FIG. 1 is a schematic, cross-sectional diagram of an illustrative embodiment of a system for treating a tissue site with reduced pressure.

FIG. 1 is a schematic diagram of a reduced-pressure therapy system 100 for treating a tissue site 102 illustrating details that may be associated with some embodiments. The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desirable to add or promote the growth of additional tissue. For example, negative-pressure therapy may be used in certain tissue areas to grow additional tissue that may be harvested and transplanted to another tissue location. The tissue site 102 may be a wound that extends through an epidermis 112, through a dermis 116, and into a subcutaneous tissue 118. The tissue site 102 may include a portion of the epidermis 112 that may be intact and may surround the tissue site 102. Treatment of the tissue site 102 may include removal of fluids, for example, exudate or ascites.

The reduced-pressure therapy system 100 may include a drape 206, a manifold 122, and a connector 128. The drape 206 may have a plasma layer 208 and an adhesive layer 210 and be disposed over the manifold 122 and the portion of the epidermis 112 surrounding the tissue site 102 to form a sealed therapeutic space 124. The drape 206 may have an aperture permitting fluid communication with the sealed therapeutic space 124 through the drape 206. The manifold 122 may be disposed within the sealed therapeutic space 124 proximate the tissue site 102. The connector 128 may be coupled to the drape 206 and be configured to provide fluid communication through the drape 206 to the sealed therapeutic space 124. The reduced-pressure therapy system 100 may further include a reduced-pressure source 126 and a negative-pressure conduit, such as a tube 130, fluidly coupled to the connector 128.

The manifold 122 is a substance or structure that may be provided to apply or distribute reduced pressure to the tissue site 102 and also to remove fluids from the tissue site 102. The manifold 122 may include a plurality of flow channels or pathways that can distribute fluids provided to and removed from the tissue site 102 in response to the application of reduced pressure. In one illustrative embodiment, the flow channels or pathways are interconnected to improve distribution of fluids provided to or removed from the tissue site 102. The manifold 122 may include a biocompatible material that is capable of being placed in contact with the tissue site 102 to distribute reduced pressure to the tissue site 102. The manifold 122 may also be one or more devices that have structural elements arranged to form flow channels. In some illustrative examples, the structural elements may be cellular foam, open-cell foam, porous tissue collections, liquids, gels, and other foams that include, or can be cured to include, flow channels. The manifold 122 may also include porous material, such as foam, gauze, felted mat, or other material suited to a particular biological application. The manifold 122 may further include porous foam that may have a plurality of interconnected cells or pores that act as flow channels. The porous foam of the manifold 122 may be a polyurethane, open-cell, reticulated foam such as GranuFoam® material manufactured by Kinetic Concepts, Incorporated of San Antonio, Tex. In other illustrative embodiments, the manifold 122 may be formed of a bioresorbable material or a scaffold material. In some situations, the manifold 122 may also be used to distribute fluids such as medications, anti-bacterials, growth factors, and various solutions to the tissue site 102.

The reduced-pressure source 126 provides reduced pressure. "Reduced pressure" generally refers to a pressure less than a local ambient pressure, such as the ambient pressure in a local environment external to a sealed therapeutic environment provided by the sealed therapeutic space 124. In many cases, the local ambient pressure may also be the atmospheric pressure at which a patient is located. Alternatively, the pressure may be less than a hydrostatic pressure associated with tissue at the tissue site. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The fluid mechanics of using a negative-pressure source to reduce pressure in another component or location, such as within a sealed therapeutic environment, can be mathematically complex. However, the basic principles of fluid mechanics applicable to reduced-pressure therapy are generally well-known to those skilled in the art, and the process of reducing pressure may be described illustratively herein as "delivering," "distributing," or "generating" reduced pressure, for example.

The reduced-pressure source 126 may be a suitable device for supplying reduced pressure, such as a vacuum pump, wall suction, micro-pump, or other source. In an illustrative embodiment, the reduced-pressure source 126 may be an electrically-driven vacuum pump. In another illustrative embodiment, the reduced-pressure source 126 may be a manually-actuated or manually-charged pump that does not require electrical power. Reduced pressure may also be generated by a device, for example, a micro-pump, directly coupled to the drape 206. The reduced-pressure source 126 may be other types of reduced-pressure pumps, or may be a wall suction port such as those available in hospitals and other medical facilities. While the amount and nature of reduced pressure applied to the tissue site 102 may vary according to the application, reduced pressure may be between −5 mm Hg (−667 Pa) and −500 mm Hg (−66.7 kPa), and more typically between −75 mm Hg (−9.9 kPa) and −200 mm Hg (−26.66 kPa).

In general, components of the reduced-pressure therapy system 100 may be coupled directly or indirectly. For example, the reduced-pressure source 126 may be directly coupled to the connector 128 and indirectly coupled to the manifold 122 through the connector 128. Components may be fluidly coupled to each other to provide a path for transferring fluids (i.e., liquid and/or gas) between the components. The connector 128 may also have a port to receive the tube 130 for fluid coupling between the tube 130 and the connector 128. In one illustrative embodiment, the connector 128 may be a T.R.A.C.® Pad or Sensa T.R.A.C.® Pad available from KCl of San Antonio, Tex. The connector 128 may allow reduced pressure to be delivered to the sealed therapeutic space 124. In other illustrative embodiments, the connector 128 may also be a conduit inserted through the drape 206.

A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, pneumatic, thermal, electrical, or chemical coupling (such as a chemical bond) in some contexts. For example, the tube 130 may be a multi-lumen conduit having a primary lumen and a secondary lumen. In an illustrative embodiment, the tube 130 may supply reduced pressure through the primary lumen and may sense pressure through the secondary lumen. The tube 130 may have a variety of shapes and include multiple primary and secondary lumens. The tube 130 may fluidly communicate with the sealed therapeutic space 124 through the connector 128 to supply the sealed therapeutic space 124 with reduced pressure and sense pressure at the tissue site 102. Reduced pressure developed by the reduced-pressure source 126 may be delivered through the tube 130 to the connector 128.

In general, exudates and other fluids flow toward lower pressure along a fluid path, a phenomenon often referred to as "suction" or "vacuum." This orientation is generally presumed for purposes of describing various features and components of reduced-pressure therapy systems herein. Thus, the term "downstream" typically implies something in a fluid path relatively closer to a negative-pressure source, and conversely, the term "upstream" implies something relatively further away from a negative-pressure source. Similarly, it may be convenient to describe certain features in terms of fluid "inlet" or "outlet" in such a frame of reference. However, the fluid path may also be reversed in some applications (such as by substituting a positive-pressure source for a negative-pressure source) and this descriptive convention should not be construed as a limiting convention.

In general, reduced-pressure therapy can be beneficial for wounds of all severity. Often, the effectiveness of reduced-pressure therapy may be limited due to the inability of the drape 206 to conform to the tissue site 102 while still providing a seal between the drape 206 and the epidermis 112. Polyurethane films are often used to form medical drapes due to polyurethane's ability to be breathable, flexible, robust, printed or colored, and provided in a range of thicknesses. Polyurethane film layers also bond well to most adhesives. Traditionally, polyurethane film layers are used to cover tissue sites and an adhesive is used to secure the polyurethane film layer to the tissue site. The challenges for using polyurethane films in medical drape applications is to balance between conformability, adhesion, sealing, breathability, robustness, and cost. Currently, most medical drapes have film layers with a thickness ranging from at least about 15 microns to about 50 microns and, typically, between about 25 microns and about 45 microns. The manufacturing process for drapes having a polyurethane film layer and an adhesive is well understood and repeatable.

A medical drape functions to enclose and protect a tissue site, maintain a moist environment within a sealed therapeutic space, act as a barrier to infectious agents, and provide a seal, particularly where reduced-pressure therapy may be utilized. When low-leak or no-leak reduced-pressure therapies are used, the ability of the medical drape to seal to the tissue site and maintain the reduced pressure at a desired level within the sealed therapeutic space becomes more critical. To improve sealing of a medical drape, a thicker adhesive may be required. Medical drapes may commonly be formed from a polyurethane film layer and an adhesive layer. The adhesive, which may be acrylic-based, may have a coating coverage of the polyurethane film between about 15 $g/m^2$ (gsm) up to about 65 gsm. A coating coverage between about 15 gsm and about 65 gsm equates to an adhesive layer thickness ranging between about 15 microns and 65 microns for medical applications. The thicker adhesives, that is adhesives having a thickness closer to about 65 microns, and a polyurethane film layer having a standard thickness of 25 microns or more, may be useful for low-leak or no-leak reduced pressure applications. Medical drapes formed with a thicker adhesive may be 50% thicker than a standard medical drape with a nominal coating of adhesive.

Figure 5A:
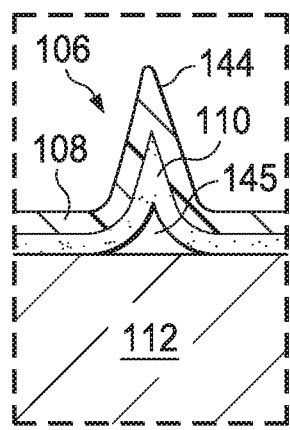
FIG. 5A is a detail in cross section of a portion of the system of FIG. 1 with another drape.

However, medical drapes having a thicker adhesive layer may have an increased size and an increased structural complexity that may give rise to increased manufacturing costs. Medical drapes having a thicker adhesive may also negatively effect conformability and breathability. To overcome these problems, a medical drape may have a thinner polyurethane film layer. For example, a polyurethane film layer approximately 10 microns or less may be used. However, polyurethane films having a thickness of approximately 10 microns or less are prone to stretching, creasing or wrinkling, and tearing during manufacturing. The creases or wrinkles may create leakage problems. For example, FIG. 5A is a sectional view of a drape 106 illustrating additional details of a medical drape having a thinner polyurethane film layer and thicker than standard adhesive layer. The drape 106 may be formed from a polyurethane film layer 108 having a thickness of about 10 microns and a thicker than standard adhesive 110 is shown. When the drape 106 is positioned at the tissue site 102 over the manifold 112, a crease 144 is formed. The crease 144 may be formed due to increased handling challenges caused by the thinner polyurethane film and may create a gap 145. The adhesive layer 210 may not be thick enough to fill in the gap 145 without compromising breathability and conformability.

In addition, to creases and wrinkles, the thinner polyurethane film may also be subject to stretching and tearing during the process of manufacturing, particularly, during the application of the adhesive to the polyurethane film. Good tension control of the polyurethane film is required during this process and is often hard to achieve. Furthermore, thinner polyurethane films are more sensitive to environmental conditions, for example, temperature and humidity, which can increase the difficulty of the manufacturing process. Other environmental processes, such as the temperature of the adhesive during manufacturing of the medical drape and the chemical make-up of the adhesive can drastically affect the ability to handle the polyurethane film during the application of the adhesive to manufacture the medical drape.

Efforts to use thinner polyurethane films less than about 15 microns have also not resolved the problems because such film layers, especially those having a thickness of about 5 microns, are susceptible to the risk of pin-holing defects. Pin-holing is the forming of microscopic openings or tears in the flexible film that may cause the film layer, and consequently the medical drape, to fail. In addition, the polyurethane film thickness must be maintained to aid in handling of the medical drape as thinner polyurethane films may make the medical drape more difficult to apply. It is also known that some adhesives, such as acrylic adhesives, significantly reduce the moisture vapor transmission rate (MVTR) of a medical drape as the adhesive layer increases in thickness. Because of these problems, polyurethane film layers having a thickness of 5 microns have not been available for medical drape applications especially for low-leak or no-leak applications of reduced-pressure therapy. Because of the unavailability of such thin film layer polyurethane, the adhesive layer has remained relatively thin, between approximately 15 microns and approximately 65 microns, to maintain an acceptable MVTR.

As disclosed herein, the reduced-pressure therapy system 100 overcomes these challenges and others by providing the drape 206 having the adhesive 210 with a plasma treated surface to form the plasma layer 208. In addition, the drape 206 may provide the thicker adhesive 210 without affecting breathability, conformability or cost.

Figure 2:
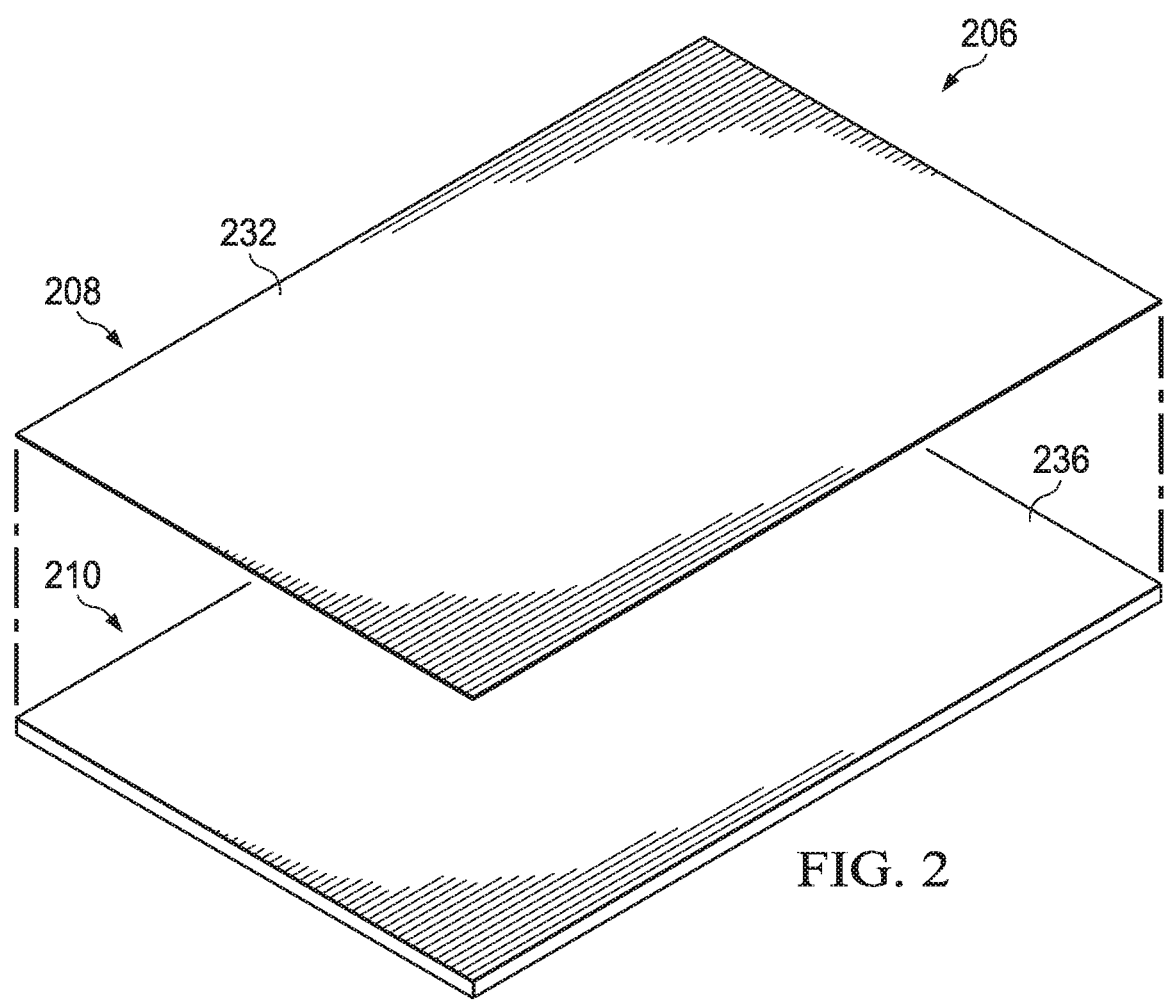
FIG. 2 is an exploded perspective view of an illustrative embodiment of a drape of FIG. 1.

FIG. 2 is a perspective exploded view of the drape 206 illustrating additional details that may be associated with some embodiments. As shown in FIG. 2, the drape 206 may have the adhesive 210 having a thickness of about 600 microns and the plasma layer 208 having a thickness of about 5 microns. The plasma layer 208 may be a non-adhesive layer formed from a portion of the adhesive 210. The plasma layer 208 may have a first side 232, and the adhesive 210 may have a first side 236.

Figure 3:
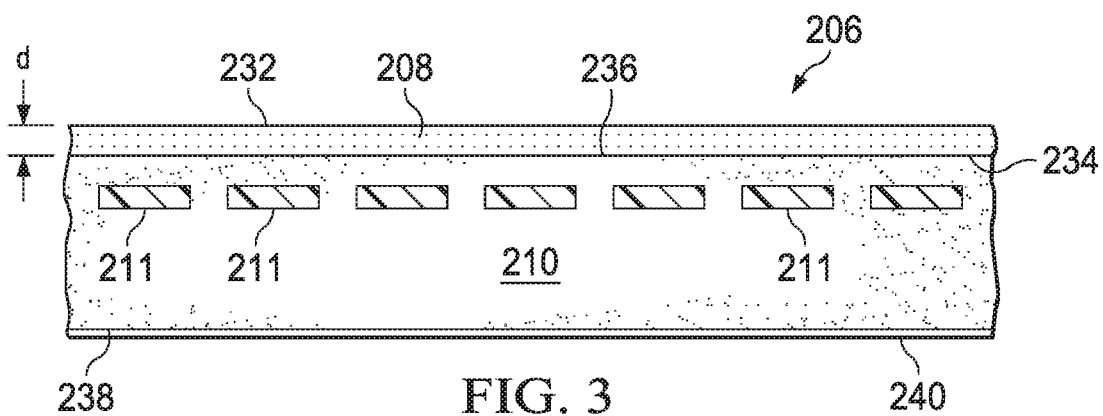
FIG. 3 is a cross-sectional view of the drape of FIG. 2.

FIG. 3 is a sectional view of the drape 206 illustrating additional details that may be associated with some embodiments. As shown, the plasma layer may have a second side 234, and the adhesive 210 may have a second side 238. In an illustrative embodiment, the second side 234 of the plasma layer 208 and the first side 236 of the adhesive 210 may form a boundary layer between the plasma layer 208 and the adhesive 210. As shown, the boundary layer between the second side 234 of the plasma layer 208 and the first side 236 of the adhesive 210 may be a distance "d" from the first side 232 of the plasma layer 208. In an embodiment, the distance "d" may be up to about 5 microns in thickness, that is less than about 5 microns. The plasma layer 208 may be a portion of the adhesive 210 treated in a plasma process to activate a monomer, such as a fluorocarbon or a silicone, within the adhesive of the adhesive 210. The plasma process may cause a chemical reaction between the monomer and the silicone gel to produce a thin, tough, non-tacky film up to 5 microns thick. Other monomer systems, such as urethane monomers and acrylic monomers, may be used with the plasma treatment process described below to produce the plasma layer 208.

The adhesive 210 may be a medically-acceptable, pressure-sensitive adhesive. The adhesive 210 may be a silicone polymer, polyurethane, polyolefin, or an additional acrylic adhesive. The adhesive 210 may also be a gel or hydrocolloid based adhesive. In some embodiments, the bond strength of the adhesive 210 may have a peel adhesion or resistance to being peeled from a stainless steel material between about 0.5N/25 mm to about 1.5N/25 mm on stainless steel substrate at 23® C. at 50% relative humidity based on ASTM D3330. The adhesive 210 may have a tackiness such that the adhesive 210 may achieve the bond strength described above after a contact time of less than about 60 seconds. In a non-limiting illustrative example, the adhesive 210 comprises a silicone adhesive with a coating weight between about 80 grams/m$^2$ (gsm) and about 400 gsm. The adhesive 210 may be up to about 600 microns in thickness/gsm.

The adhesive 210 may also have a scrim layer 211 disposed proximate the first side 236. The scrim layer 211 may be separated from the first side 236 so that the scrim layer 211 may be embedded within the adhesive 210 below the boundary layer of the second side 234 of the plasma layer 208 and the first side 236 of the adhesive 210. As described in more detail below, the plasma treatment process that forms the plasma layer 208 does not interact with the scrim layer 211. The scrim layer 211 may be a reinforcement layer embedded within the adhesive to provide extra support where the adhesive may have low strength and the plasma layer 208 does not provide a sufficient strength to limit inadvertent break down of the drape 206. The scrim layer 211 may be formed from a non-woven polymer, such as polyurethane, and may be thin and light weight with density of up to about 10 gsm. The scrim layer 211 may be more flexible than the thinnest polyurethane films available for medical drapes. Currently the thinnest polyurethane films available may be about 15 microns in thickness. The scrim layer 211 may be formed from hydrophilic materials, such as alginate or superabsorbent materials, to enable less breathable polymer adhesives, such as silicone, to manage moistures without needing perforations.

The drape 206 may include a release liner 240, disposed on the second side 238 of the adhesive 210 during the manufacturing, shipping, and storage of the drape 206. The release liner 240 may be removed prior to use of the drape 206. The release liner 240 may be a polymeric or paper based web. The release liner 240 covers the second side 238 of the adhesive 210 prior to application of the drape 206 to the tissue site 102. The release liner 240 preserves the adhesiveness of the adhesive 210 prior to contact between the adhesive 210 and the epidermis 112. The release liner 240 also prevents fluid from contacting the adhesive 210 prior to application of the drape 206 to the tissue site 102. The release liner 240 may be formed from a gas or liquid impermeable material to prevent the adhesive 210 from being contaminated or transforming to a gelatinous or liquid state before being applied to the tissue site 102. The release liner 240 may also have tabs that may aid in removal of the release liner 240 from the adhesive 210.

The drape 206 may substantially prevent the leakage of fluids, for example, through the space between the drape 206 and the tissue site 102, while allowing vapor to egress through the drape 206. The drape 206 maintains a suitable MVTR where the adhesive 210 contracts the epidermis 112 to aid in healing of the tissue site 102 when reduced-pressure therapy is applied to the tissue site 102. The drape 206 also may be formed from a material that is suitably releasable from the epidermis 112 to minimize or reduce any pain to the patient resulting from the removal of the drape 206 from the tissue site 102. While the drape 206 may be releasable, the drape 206 may maintain an adequately strong mechanical connection to the tissue site 102 as a function of the bonding characteristics of the adhesive 210.

Figure 4:
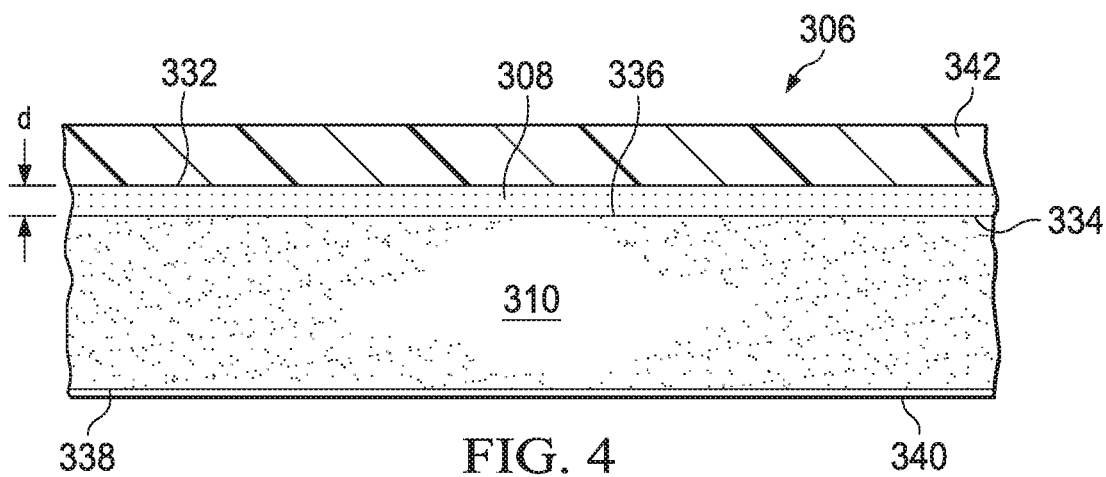
FIG. 4 is a cross-sectional view of another embodiment of the drape of FIG. 2.

FIG. 4 is a schematic side view illustrating details of another drape 306 that may be associated with some embodiments. The drape 306 may be similar to the drape 206 and used in place of the drape 206 with the reduced-pressure therapy system 100 of FIG. 1. The drape 306 may be analogous in many respects to the drape 206 of FIG. 3, and analogous components have been indicated by indexing the reference numerals by 100. The drape 306 includes a plasma layer 308 and an adhesive 310. The plasma layer 308 may be a non-adhesive layer formed from a portion of the adhesive 310. The plasma layer 308 includes a first side 332 and a second side 334. The adhesive 310 includes a first side 336 and a second side 338. In the illustrated embodiment, the second side 334 of the plasma layer 308 and the first side 336 of the adhesive 310 may form a boundary layer between the plasma layer 308 and the adhesive 310. As shown, the boundary layer between the second side 334 of the plasma layer 308 and the first side 336 of the adhesive 310 may be a distance "d" from the first side 332 of the plasma layer 308. In an embodiment, the distance "d" may be up to about 5 microns in thickness, that is less than about 5 microns. The plasma layer 308 is a portion of the adhesive 310 treated in a plasma process to activate a monomer, such as a fluorocarbon or a silicone, within the adhesive 310. The plasma process causes a chemical reaction between the monomer and the silicone gel to produce a thin, tough, non-tacky film up to 5 microns thick. Other monomer systems, such as urethane monomers and acrylic monomers, may be used with the plasma treatment process described below to produce the plasma layer 308.

The adhesive 310 may be a medically-acceptable, pressure-sensitive adhesive. The adhesive 310 may be a silicone polymer, polyurethane, polyolefin, or an additional acrylic adhesive. In some embodiments, the bond strength of the adhesive 310 may have a peel adhesion or resistance to being peeled from a stainless steel material between about 0.5N/25 mm to about 1.5N/25 mm on stainless steel substrate at 33° C. at 50% relative humidity based on ASTM D3320. The adhesive 310 may have a tackiness such that the adhesive 310 may achieve the bond strength described above after a contact time of less than 60 seconds. In a non-limiting illustrative example, the adhesive 310 comprises a silicone adhesive with a coating weight of 80 gsm to 400 gsm. The adhesive 310 may be up to about 600 microns in thickness/gsm.

The drape 306 may include a release liner 340, disposed on the second side 338 during the manufacturing, shipping, and storage of the drape 306. The release liner 340 may be removed prior to use of the drape 306. The release liner 340 covers the second side 338 of the adhesive 310 prior to application of the drape 306 to tissue site 103. The release liner 340 preserves the adhesiveness of the adhesive 310 prior to contact between the adhesive 310 and epidermis 113. The release liner 340 also prevents fluid from contacting the adhesive 310 prior to application of the drape 306 to tissue site 102. The release liner 340 may be formed from a gas or liquid impermeable material to prevent the adhesive 310 from being contaminated or transforming to a gelatinous or liquid state before being applied to tissue site 102. The release liner 340 may also have tabs that may aid in removal of the release liner 340 from the adhesive 310.

The drape 306 may also include a support layer 342 disposed on the first side 332 of the plasma layer 308. The support layer 342 may be a film layer laminated to the plasma layer 308 following the plasma treatment process described below. The support layer 342 may provide extra support to limit inadvertent break down during shipping and storage of the drape 306. Following placement of the drape 306 as described above with respect to FIG. 4, the support layer 342 may be removed from the drape 306. The support layer 342 may also have tabs that may aid in removal of the support layer 342 from the adhesive 310.

The drape 206 and the drape 306 do not experience pin-holing as the drape 206 and the drape 306 do not have a film portion like other medical drapes. In addition, the drape 206 and the drape 306 may be highly flexible and more easily conform to the tissue site 102. Still further, the overall breathability of the drape 206 and the drape 306 may be increased over other medical drapes as the overall thickness of the drape 206 and the drape 306 is reduced compared to a standard medical drape, increasing the MVTR. The drape 206 and the drape 306 may be less expensive to produce and produce less waste as fewer materials are used in their construction describe in more detail below.

FIG. 5A is a schematic cross sectional view of a portion of the reduced-pressure therapy system 100 of FIG. 1 using the common drape 106 having the film layer 108 between about 25 microns and about 45 microns and the adhesive 110. When the drape 106 is applied to the tissue site 102, the drape 106 may be stretched to conform the drape 106 to the tissue site 102 and ensure that the drape 106 seals to the intact the epidermis 112 surrounding the tissue site 102. When the force stretching the drape 106 during application is released, the drape 106 may contract, causing the wrinkle or the crease 144 to form where the drape 106 is coupled to the epidermis 112. The crease 144 pulls both the film layer 108 and the adhesive 110 away from the epidermis 112, and due to the thickness of the film layer 108, the adhesive 110 is not sufficiently strong or thick enough to close the gap 144 between the drape 106 and the epidermis 112. Thus, the crease 144 causes leaks that reduce the efficiency of the reduced-pressure therapy system 100.

Figure 5B:
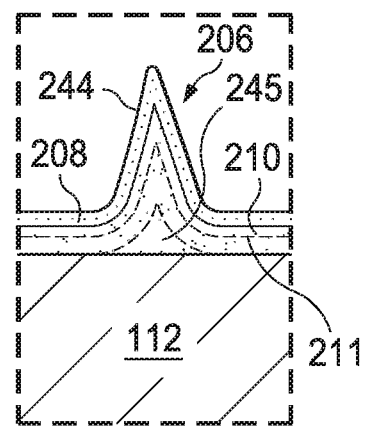
FIG. 5B is a detail in cross section of the portion of the system of FIG. 5A with the drape of FIG. 3.

FIG. 5B is a schematic cross sectional view of a portion of the reduced-pressure therapy system 100 of FIG. 1 illustrating additional details of the drape 206. The adhesive 210 may couple the drape 206 to the epidermis 112. During the application of the drape 206 to the epidermis 112, the drape 206 may form a crease or a wrinkle 244. The crease 244 may cause a portion of the drape 206 to be pulled away from the epidermis 112. This may also cause a portion of the adhesive 210 to pull away from the epidermis 112 as described above. However, because the drape 206 includes the plasma layer 208, being between about 5 microns and about 15 microns, and the adhesive 210, being between about 80 microns and about 600 microns, the adhesive 210 will not pull away from the epidermis 112 to form a gap 245 as shown by the dashed lines. Rather, the adhesive 210 fills the entire void under the crease 244 to prevent a leak. The adhesive 210 may fill the gap 245 between the plasma layer 208 and the epidermis 112, thereby limiting the formation of leaks that may prevent proper operation of the reduced-pressure therapy system 100. In addition, a height of the crease 244 may be lower with the drape 206 than with the drape 106. Thus, the drape 206 may substantially prevent leakage of fluid through the space between the drape 206 and the epidermis 112, while maintaining a high MVTR and increased conformability.

Figure 6:
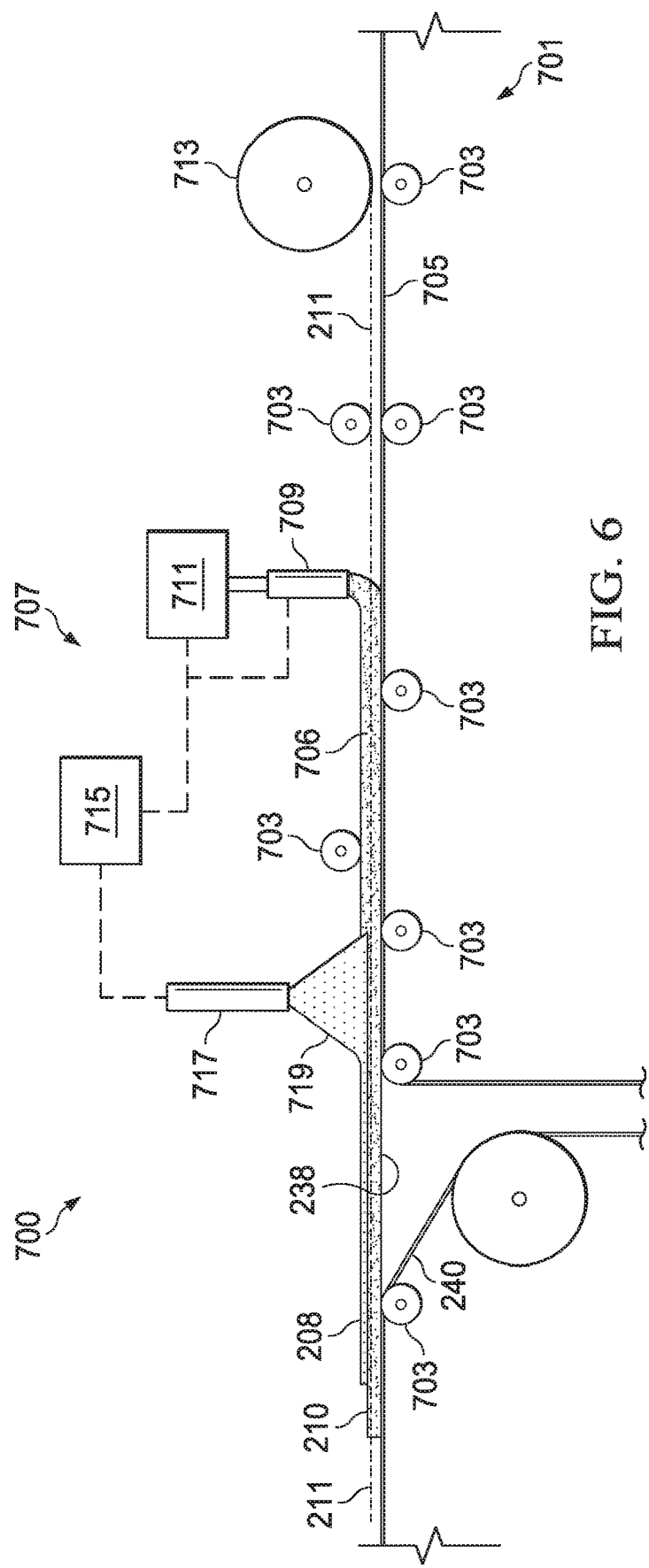
FIG. 6 is a schematic diagram of a manufacturing apparatus of the drape of FIG. 3.

FIG. 6 is a schematic diagram of an extrusion apparatus 700 illustrating additional details associated with the manufacturing of the drape 206 of FIG. 3. The extrusion apparatus 700 includes a conveyor assembly 701, and an extrusion assembly 707. The scrim layer 211 may be provided on the conveyor assembly 701. The conveyor assembly 701 may include one or more rollers 703 on which the scrim layer 211 may be disposed. Generally, the rollers 703 may support the scrim layer 211 and may be motorized or otherwise powered so that the scrim layer 211 may move through the conveyor assembly 701. The conveyor assembly 701 may include other conveyance devices, for example a conveyor belt, gravity conveyor, bucket conveyor, roller conveyor, chain conveyor, vibrating conveyor, or the like, configured to transport the drape 206 through the extrusion apparatus 700. The conveyor assembly 701 may be one or more conveyance systems or a single conveyor system as schematically illustrated in FIG. 6. In an illustrative embodiment, the scrim layer 211 may be provided to the conveyor assembly 701 in sheets that appear continuous to the conveyor assembly 701 during operation of the conveyor assembly 701. For example, the scrim layer 211 may be provided in rolls 713 that may be disposed onto the conveyor assembly 701 and unrolled by the conveyor assembly 701. For example, the conveyor assembly 701 may move a first end of the scrim layer 211 through the extrusion apparatus 700, unrolling the roll 713. The scrim layer 211 may be disposed on the conveyor assembly 701 so that the scrim layer 211 may be proximate a belt 705 of the conveyor assembly 701. In an illustrative embodiment, the scrim layer 211 may be separated from the belt 705 a predetermined distance so that the scrim layer 211 may not contact the belt 705. For example, the scrim layer 211 may be provided to the conveyor assembly 701 so that the scrim layer 211 may be separated from the belt 705 a distance of about 600 microns. In other embodiments, the scrim layer 211 may be provided to the conveyor assembly 701 so that the scrim layer 211 may be separated from the belt 705 a distance between about 500 microns and about 600 microns.

The conveyor assembly 701 may convey the scrim layer 211 through the extrusion assembly 707. The extrusion assembly 707 can include one or more adhesive extruders, such as an adhesive extruder 709, an adhesive supply 711, a control system 715, and a plasma jet assembly 717. The adhesive extruder 709 may be a slot die fluidly coupled to the adhesive supply 711 for the supply of the adhesive to the adhesive extruder 709. The control system 715 is communicatively coupled to the adhesive extruder 709 and the adhesive supply 711 to operate the extrusion assembly 707 as disclosed herein. The control system 715 is also communicatively coupled to the plasma jet assembly 717 for operation of the plasma jet assembly 717 as disclosed herein.

The control system 715 may include programmable logic controllers, data processing systems, or the like, configured to receive input from the above listed devices and communicate with those same devices for operation thereof. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code may be retrieved from bulk storage during execution. The adhesive extruder 709 may be coupled to respective motorized controllers and operable for motion relative to an initial position as disclosed herein. The motorized controllers may be a suitable device configured to receive operative signals or instructions from the control system 715.

The control system 715 may include discreet input/output devices that may be suitable devices such as pneumatic sensors, temperature sensors, or the like configured to communicate signals to the control system 715. Input/output or I/O devices (including but not limited to keyboards, displays, pointing devices, etc.) can be coupled to the system either directly or through intervening I/O controllers. Network adapters, such as a modem or ethernet card, may also be coupled to the control system 715 to enable the control system 715 to become coupled to other data processing systems or remote printers or storage devices through intervening private or public networks.

The adhesive extruder 709 is disposed proximate the belt 705 of the conveyor assembly 701. The adhesive extruder 709 may include a valve and a die configured to extrude the adhesive onto the belt 705 as a sheet of adhesive material 706. The adhesive extruder 709 deposits the sheet of adhesive material 706 onto the belt 705 so that the thickness of the sheet of adhesive material 706 may be greater than distance between the belt 705 and the scrim layer 211. In an illustrative embodiment, the scrim layer 211 is separated from a surface of the sheet of adhesive material 706 opposite the belt 705 a distance of about 5 microns to about 10 microns. In another illustrative embodiment, the sheet of adhesive material 706 may be deposited on the belt 705 with a thickness of about 600 microns.

In some embodiments, the sheet of adhesive material 706 is subjected to heat or ultraviolet light following extrusion of the sheet of adhesive material 706 on the belt 705. Heating the sheet of adhesive material 706 or subjecting the sheet of adhesive material 706 to ultraviolet light crosslinks the sheet of adhesive material 706. Crosslinking causes the sheet of adhesive material 706 to form a gel adhesive. In the illustrative process, the gel adhesive is a silicone gel adhesive. Crosslinking builds a chemical bridge between the polymer chains that make up the sheet of adhesive material 706. Crosslinking may reduce the adhesiveness of the sheet of adhesive material 706.

The sheet of adhesive material 706 and the scrim layer 211 may be conveyed past the plasma jet assembly 717. The plasma jet assembly 717 may be an apparatus configured to conduct a plasma treatment process on the surface of the sheet of adhesive material 706. In an illustrative plasma treatment process, the plasma jet assembly 717 receives a gas and passes the gas between a nozzle that includes a cathode and an anode. An arc between the cathode and the anode ionizes the gas and causes the gas to dissociate and form a plasma stream 719. The sheet of adhesive material 706, having the scrim layer 211 disposed therein, passes through the plasma stream 719 as illustrated in FIG. 6. The plasma stream 719 heats the surface of the sheet of adhesive material 706, activating a monomer within the adhesive, such as a fluorocarbon or silicone. Activation of the monomer causes a chemical reaction that causes the sheet of adhesive material 706 to form the plasma layer 208, a thin, tough, non-tacky film up to about five microns thick. If a thicker plasma layer is desired, additional plasma treatment processes may be performed to increase the thickness of the plasma layer 208.

Other processes to form the plasma layer 208 from the sheet of adhesive material 706 may be used. For example, powder coating processes, wet coating processes, and corona discharge processes may be used to form the plasma layer 208. The corona discharge process may be used where an oxidized or highly crosslinked surface is desired. Other processes may use a talc, a polymer, a wax, or a powder emulsion, a dispersion, or a solution. Following the plasma treatment process, the sheet of adhesive material 706 includes the plasma layer 208 and the adhesive 210. The release liner 240 may then be releasably coupled to the second side 238 of the adhesive 210. The plasma treatment process may be conducted in-line as shown herein or conducted in a separate process with another conveyance assembly.

Figure 7:
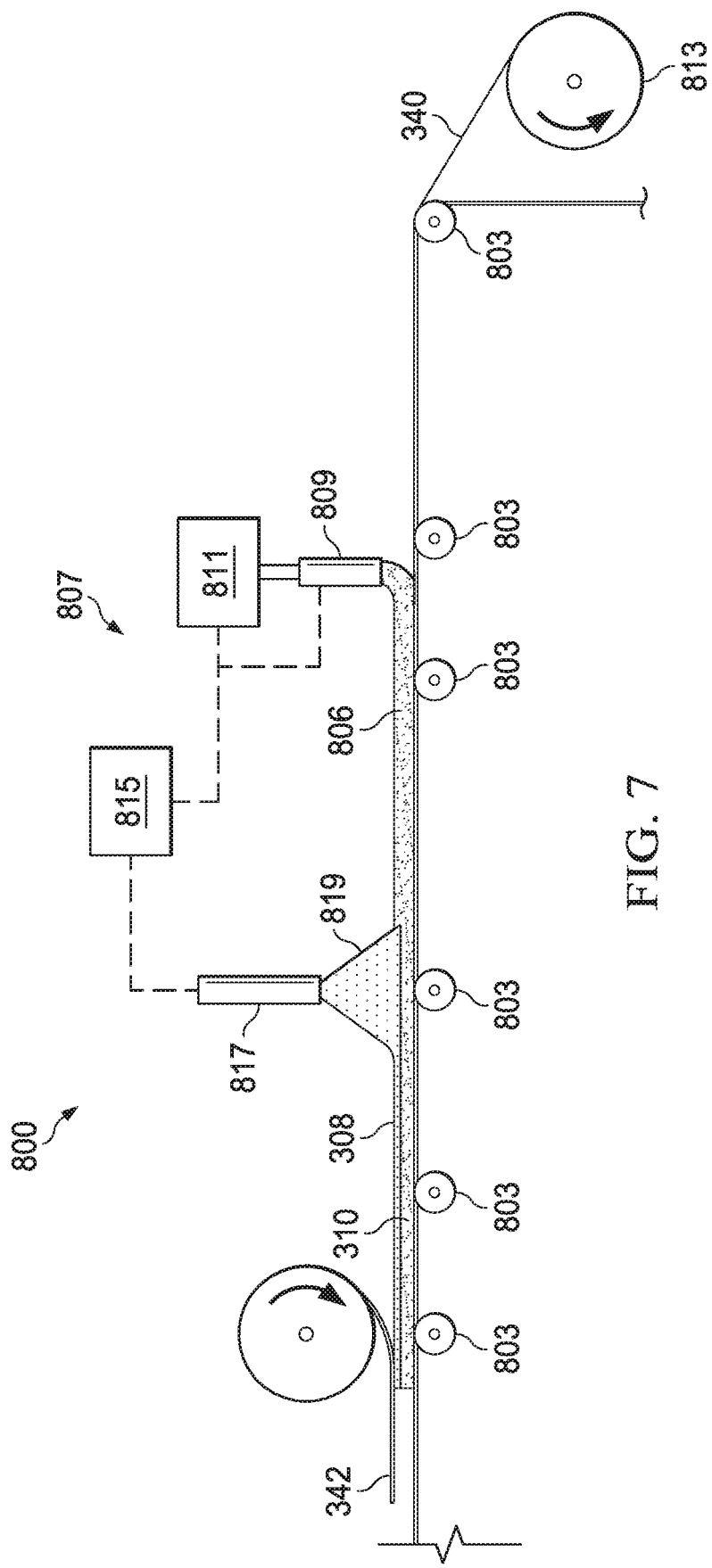
FIG. 7 is a schematic diagram of a manufacturing apparatus of the drape of FIG. 4.

FIG. 7 is a schematic diagram of an extrusion apparatus 800 for the manufacturing of the drape 306. The extrusion apparatus 800 includes a conveyor assembly 801 and an extrusion assembly 807. The release liner 340 may be provided on the conveyor assembly 801. The conveyor assembly 801 may include one or more rollers 803 on which the release liner 340 may be disposed. Generally, the rollers 803 may support the release liner 340 and may be motorized or otherwise powered so that the release liner 340 may translate on the conveyor assembly 801. The conveyor assembly 801 may include other conveyance devices, for example a conveyor belt, gravity conveyor, bucket conveyor, roller conveyor, chain conveyor, vibrating conveyor, or the like, configured to transport the drape 306 through the extrusion apparatus 800. The conveyor assembly 801 may be one or more conveyance systems or a single conveyor system as schematically illustrated in FIG. 7. In an illustrative embodiment, the release liner 340 may be provided to the conveyor assembly 801 in sheets that appear continuous to the conveyor assembly 801 during operation of the conveyor assembly 801. For example, the release liner 340 may be provided in a roll 813 that may be disposed onto the conveyor assembly 801 and unrolled by the conveyor assembly 801 as the conveyor assembly 801 moves a first end of the release liner 340 through the extrusion apparatus 800.

The conveyor assembly 801 conveys the release liner 340 through the extrusion assembly 807. The extrusion assembly 807 can include one or more adhesive extruders, such as an adhesive extruder 809, an adhesive supply 811, a control system 815, and a plasma jet assembly 817. The adhesive extruder 809 may be a slot die that is fluidly coupled to the adhesive supply 811 for the supply of the adhesive to the adhesive extruder 809. The control system 815 may be communicatively coupled to the adhesive extruder 809 and the adhesive supply 811 to operate the extrusion assembly 807 as disclosed herein. The control system 815 may also be communicatively coupled to the plasma jet assembly 817 for operation of the plasma jet assembly 817 as described herein.

The control system 815 may include programmable logic controllers, data processing systems, or the like, configured to receive input from the above listed devices and communicate with those same devices for operation thereof. A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code may be retrieved from bulk storage during execution. In some embodiments, the adhesive extruder 809 may be coupled to respective motorized controllers and operable for motion relative to an initial position as disclosed herein. The motorized controllers may be a suitable device configured to receive operative signals or instructions from the control system 815.

The control system 815 may include discreet input/output devices that may be suitable devices such as pneumatic sensors, temperature sensors, or the like configured to communicate signals to the control system 815. Input/output or I/O devices (including but not limited to keyboards, displays, pointing devices, etc.) can be coupled to the system either directly or through intervening I/O controllers. Network adapters, such as a modem or ethernet card, may also be coupled to the control system 815 to enable the control system 815 to become coupled to other data processing systems or remote printers or storage devices through intervening private or public networks.

The adhesive extruder 809 is disposed proximate the release liner 340 on the conveyor assembly 801. The adhesive extruder 809 may include a valve and a die configured to extrude the adhesive onto the release liner 340 as a sheet of adhesive material 806. The adhesive extruder 809 deposits the sheet of adhesive material 806 onto the release line 340 so that the thickness of the sheet of adhesive material 806 may be about 600 microns thick.

In an embodiment, the sheet of adhesive material 806 is subjected to heat or ultraviolet light following extrusion of the sheet of adhesive material 806 onto the release liner 340. Heating the sheet of adhesive material 806 or subjecting the sheet of adhesive material 806 to ultraviolet light crosslinks the sheet of adhesive material 806. Crosslinking causes the sheet of adhesive material 806 to form a gel adhesive. In an illustrative embodiment, the gel adhesive may be a silicone gel adhesive. Crosslinking may build a chemical bridge between the polymer chains that make up the sheet of adhesive material 806, reducing the adhesiveness of the sheet of adhesive material 806.

The sheet of adhesive material 806 and the release liner 340 may be conveyed past the plasma jet assembly 817. The plasma jet assembly 817 may be an apparatus configured to conduct a plasma treatment process on the surface of the sheet of adhesive material 806. In an illustrative plasma treatment process, the plasma jet assembly 817 receives a gas and passes the gas between a nozzle that includes a cathode and an anode. An arc between the cathode and the anode ionizes the gas and causes the gas to dissociate and form a plasma stream 819. The sheet of adhesive material 806 and the release liner 340 may pass through the plasma stream 819 as illustrated in FIG. 7. The plasma stream 819 may heat the surface of the sheet of adhesive material 806, activating a monomer within the adhesive, such as a fluorocarbon or silicone. Activation of the monomer may cause a chemical reaction that causes the sheet of adhesive material 806 to form the plasma layer 308, a thin, tough, non-tacky film up to about five microns thick. If a thicker plasma layer is desired, additional plasma treatment processes may be performed to increase the thickness of the plasma layer 308.

The manufacturing apparatuses described above with respect to specific embodiments of the drape 206 and the drape 306 may be used to manufacture the embodiments of FIGS. 2-4, as well as variations thereof. In addition, other manufacturing methods employed to produce a thick transfer adhesive or adhesive coated film may be used to construct the drapes described herein, particularly where the adhesive is a gel or hydrocolloid based adhesive. In some embodiments, the rheology of the adhesives may be modified in a suitable manner to reduce the amount of flow during the manufacturing processes and curing or drying to prevent adhesive migration onto undesired areas.

In other embodiments, the adhesives may be mixed with blowing or expanding agents, for example organic and inorganic low temperature boiling point liquids. The blowing or expanding agents allow for the adhesives to expand under the application of heat or light to increase the thickness of the adhesive following deposition by one of the above described processes. The blowing or expanding agents may reduce the amount of adhesive needed and decrease the cost of production and the cost of the resulting medical drape. In some embodiments, the application of heat or light may be delayed until application of the medical drape to the epidermis so that the contact area with the epidermis increases as the adhesive may be warmed by contact with the epidermis. The application of light or heat following application of the medical drape to the epidermis may provide a better seal of the medical drape to the epidermis while retaining strong bonding characteristics.

The medical drapes and their equivalents as described above may be thinner than standard drapes, may have high MVTRs, and may be highly flexible and conformable. In addition, they may have reduced instances of leaks due to their increase adhesive thickness. Still further the medical drapes and their equivalents described herein may have a lower production cost. The medical drapes and their equivalents herein may also be subject to simpler application and high breathability, increasing their usefulness in evaporative dressings. In addition, embodiments without a support layer may simplify application and reduce waste.

Although certain embodiments and their advantages have been disclosed in the context of certain illustrative, non-limiting embodiments, it should be understood that various changes, substitutions, permutations, and alterations can be made without departing from the scope of the invention as defined by the appended claims. It will be appreciated that features that may be described in connection to one embodiment may also be applicable to other embodiments. It will also be understood that the benefits and advantages described above may relate to one embodiment or may relate to several embodiments. It will further be understood that reference to "an" item refers to one or more of those items.

The steps of the methods described herein may be carried out in a suitable order, or simultaneously where appropriate and as otherwise understood by one skilled in the art.

Where appropriate, aspects of the embodiments described above may be combined with aspects of the other embodiments described to form further examples having comparable or different properties and addressing the same or different problems.

It will be understood that the embodiments described herein are given by way of example only and that various modifications may be made by those skilled in the art. The above specification, examples and data provide a complete description of the structure and use of exemplary embodiments. Although various embodiments have been described above with a certain degree of particularity, or with reference to one or more individual illustrations, those skilled in the art could make numerous alterations to the example embodiments without departing from the scope of the claims.

We claim:

1. A drape comprising:
   a contact layer formed of silicone and having a first surface and an opposite second surface;
   a non-adhesive layer having a thickness formed by treating the first surface of the contact layer with a plasma treatment process; and
   wherein the second surface is configured to adhere to tissue.

2. The drape of claim 1, wherein a thickness of the contact layer is between about 100 microns and about 600 microns.

3. The drape of claim 1, wherein the thickness of the non-adhesive layer is about 5 microns.

4. The drape of claim 1, wherein the non-adhesive layer has a plasma layer basis weight between about 5 grams/m$^2$ and about 15 grams/m$^2$.

5. The drape of claim 1, wherein the non-adhesive layer has a coating basis weight between about 80 grams/m$^2$ and about 400 grams/m$^2$.

6. The drape of claim 1, wherein the contact layer has a bond strength between about 0.5N/25 mm and about 1.5N/25 mm.

7. The drape of claim 1, wherein the contact layer further comprises a material configured to crosslink when exposed to an ultraviolet light source.

8. The drape of claim 1, wherein the contact layer further comprises a scrim layer.

9. A conforming tissue seal comprising:
   an adhesive layer formed of a substantially uniform silicone adhesive having a thickness greater than about 100 microns, the adhesive layer having a first surface and a second surface;
   a plasma layer having a thickness of about 5 microns formed by treating the first surface of the adhesive layer with a plasma treatment process; and
   wherein the second surface of the adhesive layer is configured to adhere to tissue.

10. The tissue seal of claim 9, wherein the thickness of the adhesive layer is between about 100 microns and about 600 microns.

11. The tissue seal of claim 9, wherein the adhesive layer has a bond strength of about 0.5N/25 mm to about 1.5N/25 mm.

12. The tissue seal of claim 9, wherein the adhesive layer further comprises a material configured to crosslink when exposed to an ultraviolet light source.

13. The tissue seal of claim 9, wherein the adhesive layer further comprises an expanding agent configured to react to a heat source.

14. The tissue seal of claim 9, wherein the adhesive layer further comprises an expanding agent configured to react to a light source.

15. The tissue seal of claim 9, wherein the adhesive layer further comprises a scrim layer.

16. A drape comprising:
   an adhesive layer formed of a silicone adhesive having a thickness greater than about 100 microns, the adhesive layer having a first surface and a second surface;
   a plasma layer having a thickness of about 5 microns formed by treating the first surface of the adhesive layer with a plasma treatment process; and
   wherein the adhesive layer is configured to draw the plasma layer toward an epidermis to fill gaps between the plasma layer and the epidermis.

17. The drape of claim 16, wherein the plasma layer has a basis weight between about 5 grams/m$^2$ and about 15 grams/m$^2$.

18. The drape of claim 16, wherein the adhesive layer has a bond strength between about 0.5N/25 mm and about 1.5N/25 mm.

19. The drape of claim 16, wherein the adhesive layer further comprises an expanding agent configured to react to a heat source.

20. The drape of claim 16, wherein the adhesive layer further comprises an expanding agent configured to react to a light source.

* * * * *